United States Patent [19]

Coy et al.

[11] Patent Number: 5,003,011

[45] Date of Patent: * Mar. 26, 1991

[54] THERAPEUTIC DECAPEPTIDES

[75] Inventors: David H. Coy, New Orleans, La.; Jacques-Pierre Moreau, Upton, Mass.

[73] Assignee: The Administrators of the Tulane Educational Fund, New Orleans, La.

[*] Notice: The portion of the term of this patent subsequent to Sep. 12, 2006 has been disclaimed.

[21] Appl. No.: 421,245

[22] Filed: Oct. 13, 1989

Related U.S. Application Data

[63] Continuation-in-part of Ser. No. 352,140, May 15, 1989, abandoned, which is a continuation of Ser. No. 65,765, Jun. 19, 1987, Pat. No. 4,866,160, which is a continuation-in-part of Ser. No. 879,338, Jun. 27, 1986, abandoned, which is a continuation-in-part of Ser. No. 798,239, Nov. 14, 1985, abandoned, which is a continuation-in-part of Ser. No. 721,330, Apr. 9, 1985, abandoned.

[51] Int. Cl.$^5$ .................. A61K 37/02; A61K 9/48; A61K 9/20; C07K 7/06
[52] U.S. Cl. .................. 530/328; 530/313; 514/15; 514/800; 514/885; 424/451; 424/464
[58] Field of Search ............ 530/313, 328; 514/800, 514/885, 15; 424/451, 464

[56] References Cited

U.S. PATENT DOCUMENTS 4,851,385 7/1989 Roeske .................. 514/15

4,866,160 9/1989 Coy et al. .................. 530/328

Primary Examiner—Nathan M. Nutter
Attorney, Agent, or Firm—Fish & Richardson

[57] ABSTRACT

A decapeptide of the formula:

$$\text{N-Ac-}A^1\text{-}A^2\text{-}A^3\text{-SER}^4\text{-}A^5\text{-}A^6\text{-}A^7\text{-}A^8\text{-}A^9\text{-}A^{10},$$

wherein each $A^1$, $A^2$, and $A^3$, independently, is D-$\beta$-Nal, D-p-X-Phe (where X is halogen, H, $NH_2$, $NO_2$, OH, or $C_{1-3}$ alkyl); $A^5$ is p-X-Phe (where X is halogen, H, $NH_2$, $NO_2$, OH, or $C_{1-3}$ alkyl); $A^6$ is D-Lys, D-Arg, $\beta$-Nal, D-$\beta$-Nal, D-Trp, D-p-X-Phe (where X is halogen, H, $NH_2$, $NO_2$, or $C_{1-3}$ alkyl) or D-lys-$\epsilon$-NH-R (where R is H, a branched or straight chain or cyclo $C_1$–$C_{10}$ alkyl group, or an aryl group); $A^7$ is p-X-Phe (where X is halogen, H, $NH_2$, $NO_2$, OH, $C_2F_5$, or $C_{1-3}$ alkyl), cyclohexyala, or Trp; $A^8$ is Arg, Lys, or Lys-$\epsilon$-NH-R (where R is H, a branched or straight chain or cyclo $C_1$–$C_{10}$ alkyl group, or an aryl croup); $A^9$ is Pro; and $A^{10}$ is D-Ala-$NH_2$, Gly-$NH_2$, D-Ser, or D-Ser-$NH_2$; provided that at least one of $A^2$ or $A^3$ must be D-Phe or D-Tyr; and further provided that one or both of $A^6$ and $A^8$ must be the following: $A^6$ must be D-Lys-$\epsilon$-NH-R (where R is H, a branched or straight chain or cyclo $C_1$–$C_{10}$ alkyl group, or an aryl group); $A^8$ must be Lys-$\epsilon$-NH-R (where R is H, a branched or straight chain or cyclo $C_1$–$C_{10}$ alkyl group, or an aryl group), or a pharmaceuticaly acceptable salt thereof.

22 Claims, 8 Drawing Sheets

THERAPEUTIC DECAPEPTIDES

This invention was made in the course of work under a grant or award from the U.S. government; therefore, the U.S. government has rights in the invention.

BACKGROUND OF THE INVENTION

This application is a continuation-in-part of U.S. Ser. No. 352,140, filed May 15, 1989, now abandoned which is a continuation of U.S. Ser. No. 065,765 filed June 23, 1987 and now U.S. Pat. No. 4,866,160 which is a continuation-in-part of U.S. Ser. No. 879,338, filed June 27, 1986 and now abandoned, continuation-in-part of U.S. Ser. No. 798,239, filed Nov. 14, 1985, now abandoned, which is a continuation-in-part of U.S. Ser. No. 721,330, filed Apr. 9, 1985, now abandoned.

This invention relates to therapeutic peptides.

A number of luteinizing hormone releasing hormone (LH-RH) analogs have been described which inhibit the release of LH-RH, a peptide hormone having the formula pGlu-His-Trp-Ser-Tyr-Gly-Leu-Arg-Pro-Gly-$NH_2$. These analogs are called LH-RH antigonists. For example, Coy et al. U.S. Pat. No. 4,431,635, hereby incorporated by reference, describes LH-RH analogs having the general formula X-$R^1$-$R^2$-$R^3$-Ser-Tyr-$R^4$-Leu-Arg-Pro-$R^5$-$NH_2$, in which X can be Ac; $R^1$ and $R^4$, independently, can be D-Trp or D-p-X-Phe, where X is a halogen or methyl group; $R^2$ can be D-p-X-Phe; $R^3$ can be D-Trp; and $R^5$ can be Gly or D-Ala.

SUMMARY OF THE INVENTION

In general, the invention features a decapeptide of the formula:

$$N\text{-}Ac\text{-}A^1\text{-}A^2\text{-}A^3\text{-}Ser^4\text{-}A^5\text{-}A^6\text{-}A^7\text{-}A^8\text{-}A^9\text{-}A^{10},$$

wherein each $A^1$, $A^2$, and $A^3$, independently, is D-$\beta$-Nal, D-p-X-Phe (where X is halogen, H, $NH_2$, $NO_2$, OH, or $C_{1-3}$ alkyl, e.g., methyl, ethyl, or n-propyl); $A^5$ is p-X-Phe (where X is halogen, H, $NH_2$, $NO_2$, OH, or $C_{1-3}$ alkyl); $A^6$ is D-Lys, D-Arg, $\beta$-Nal, D-$\beta$-Nal, D-Trp, D-p-X-Phe (where X is halogen, H, $NH_2$, $NO_2$, or $C_{1-3}$ alkyl) or D-Lys-$\epsilon$-NH-R (where R is H, a branched or straight chain or cyclo $C_1$–$C_{10}$ alkyl group, e.g., methyl, ethyl, isopropyl, heptyl, butyl, or cyclopentyl, or an aryl group, e.g., benzyl, p-Cl-benzyl, or $CH_2$-napthyl); $A^7$ is p-X-Phe (where X is halogen, H, $NH_2$, $NO_2$, OH, $C_2F_5$, or $C_{1-3}$ alkyl), cyclohexylAlanine, or Trp; $A^8$ is Arg, Lys, or Lys-$\epsilon$-NH-R (where R is H, a branched or straight chain or cyclo $C_1$–$C_{10}$ alkyl group, e.g., methyl, ethyl, isopropyl, heptyl, butyl, or cyclopentyl, or an aryl group, e.g., benzyl, p-Cl-benzyl, or $CH_2$-napthyl); $A^9$ is Pro; and $A^{10}$ is D-Ala-$NH_2$, Gly-$NH_2$, D-Ser, or D-Ser-$NH_2$; provided that at least one of $A^2$ or $A^3$ must be D-Phe or D-Tyr; and further provided that one or both of $A^6$ and $A^8$ must be the following: $A^6$ must be D-Lys-$\epsilon$-NH-R (where R is H, a branched or straight chain or cyclo $C_1$–$C_{10}$ alkyl group, or an aryl group); $A^8$ must be Lys-$\epsilon$-NH-R (where R is H, a branched or straight chain or cyclo $C_1$–$C_{10}$ alkyl group, or an aryl group), or a pharmaceutically acceptable salt thereof. ($\beta$-Nal refers to $\beta$-napthylalanine; where no L- or D- designation is given herein, the L-isomer is intended; N-Ac refers to the N-acetyl protecting group, i.e., an acetyl group attached to a terminal amino acid residue on the amine nitrogen; halogen refers to fluoro, chloro, or bromo.)

Preferred decapeptides include those wherein $A^6$ is D-Lys-$\epsilon$-NH-R (where R is H, a branched or straight chain or cyclo $C_{1-10}$ alkyl group, or an aryl group); wherein $A^8$ is Lys-$\epsilon$-NH-R (where R is H, a branched or straight chain or cyclo $C_1$–$C_{10}$ alkyl group, or an aryl group).

Other preferred decapeptides are wherein $A^1$–$A^{10}$ is
N-acetyl-D-$\beta$-Nal-D-Phe-D-Phe-Ser-Tyr-D-Arg-Phe-(isopropyl)D-Lys-Pro-D-Ala-$NH_2$;
N-acetyl-D-$\beta$-Nal-D-Phe-D-Phe-Ser-Tyr-D-(benzyl)Lys-Phe-Arg Pro-D-Ala-$NH_2$;
N-acetyl-D-$\beta$-Nal-D-Phe-D-Phe-Ser-Tyr-D-(benzyl)Lys-Phe-Arg-Pro-D-Ala-$NH_2$;
N-acetyl-D-$\beta$-Nal-D-Phe-D-Phe-Ser-Tyr-D-(heptyl)Lys-Phe-Arg-Pro D-Ala-$NH_2$;
N-acetyl-D-$\beta$-Nal-D-Phe-D-Phe-Ser-Tyr-D-(cyclopentyl)Lys-Phe-Arg-Pro-D-Ala-$NH_2$;
N-acetyl-D-$\beta$-Nal-D-Phe-D-Phe-Ser-Tyr-D-Arg-Phe-(t-butylmethyl)Lys-Pro-D-Ala-$NH_2$;
N-acetyl-D-$\beta$-Nal-D-Phe-D-Phe-Ser-Tyr-D-Arg-Phe-(4-methylbenzyl)Lys-Pro-D-Ala-$NH_2$;
N-acetyl-D-$\beta$-Nal-D-Phe-D-Phe-Ser-Tyr-D-Arg-Phe-(benzyl)Lys-Pro-D-Ala-$NH_2$;
N-acetyl-D-$\beta$-Nal-D-p-Cl-Phe-D-Trp-Ser-Tyr-D-p-$NH_2$-Phe-Phe-(isopropyl)Lys-Pro-D-Ala-$NH_2$; ;
N-acetyl-D-$\beta$-Nal-D-Phe-D-Phe-Ser-Tyr-D-(heptyl)Lys-Phe-(heptyl)Lys-Pro-D-Ala-$NH_2$;
N-acetyl-D-$\beta$-Nal-D-Phe-D-Phe-Ser-Tyr-D-(cyclopentyl)Lys-Phe-(cyclopentyl)Lys-Pro-D-Ala-$NH_2$.
N-acetyl-D-$\beta$-Nal-D-Phe-D-Phe-Ser-Tyr-D-(1-butylpentyl)Lys-Phe-(1-butylpentyl)Lys-Pro-D-Ala-$NH_2$.

In other preferred embodiments, a therapeutically effective amount of the therapeutic decapeptide and a pharmaceutically acceptable carrier substance or salt, e.g., magnesium carbonate or lactose, together form a therapeutic composition for inhibiting the release of sex hormones, particularly LH, induced by LH-RH. This composition can be in the form of a pill, tablet, capsule, liquid, or sustained release tablet for oral administration; a liquid spray for nasal administration; or a liquid for parenteral (intravenous, intramuscular, and subcutaneous) topical, vaginal, rectal, buccal (including sublingual), or intraperitoneal administration.

As used herein, the term "pharmaceutically acceptable" carrier substance or salts refers to a carrier or salt that retain the desired biological activity of the parent compound and do not impart any undesired toxicological effects. Examples of salts are (a) acid addition salts formed with inorganic acids, for example, hydrochloric acid, hydrobromic acid, sulfuric acid, phosphoric acid, nitric acid and the like; and salts formed with organic acids such as, for example, acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylene-diamine or ethylenediamine; or (c) combinations, of (a) and (b), e.g., a zinc tannate salt and the like. The most suitable route will depend upon the use, particular active ingredient, and the subject involved.

Another preferred form for administration is an injectable suspension of the peptide with a bioerodible, biocompatible polymer matrix capable of effecting sustained release of the peptide. Other suitable forms are peptide/polymer implants, transdermal patches, transmucosal patches (vaginal), and nasal spray, and compositions usable with iontophoretic techniques.

The decapeptides of the invention are active in inhibiting the LH-RH induced release of LH, and exhibit a long duration of activity, thus minimizing the amount and frequency of dosages. Furthermore, manufacture is relatively simple and inexpensive. In addition, the peptides have the advantage of being able to be administered orally, a property owing to their high lipophilicity and their ability to withstand enzymatic degradation by peptidase.

The peptides of the invention have D-X-Phe or D-Tyr at at least one of positions $A^2$ or $A^3$. D-X-Phe, D-Trp, or D-Tyr at position $A^3$ have been found to be modifications of particular importance in terms of activity, while D-Phe at position $A^2$ provides further cost reduction, compared to D-p-X-Phe at $A^2$, without significant comparative loss of activity. The presence of D-Lys-ε-NH-R at position $A^6$ and Lys-ε-NH-R at position $A^8$ when R is an alkyl or aryl group lessen the irritant effect of the decapeptide. Presumably, this is due to an observed decrease in histamine-releasing activity. It is further believed that the presence of Arg at position $A^5$ and D-Tyr at position $A^6$, known as the Hodgen modification, also decreases histamine-releasing activity. p-X-Phe at position $A^7$ is also particularly advantageous in terms of activity.

It has also been discovered that LH-RH antagonists in general, and the above-described decapeptides in particular, can be used to treat immunosuppressed patients when administered as described above. The antagonists rejuvenate the thymus, which then produces T-cells to replace T-cells lost as a result of the immunodeficiency.

The peptide antagonists of the invention can be used to treat some forms of hormone dependent cancers including breast, prostate, and ovary. Some benign conditions resulting from an overproduction of sex hormone can benefit from treatment with a peptide of the invention; e.g., benign prostatic hyperplasia, endometriosis, or lyomas. It has also been discovered that the LHRH antagonists of the invention can exhibit a direct antitumoral effect in human mammary cancer cell lines (e.g. MCF-7). Other uses include but are not limited to the following: female contraception; ovulation prevention or delay; pregnancy termination in domestic animals and pets; induction of parturition; synchronization of ovulation; estrus suppression; growth promotion in female animals; luteolysis, menses induction; therapy for premenstrual syndrome; therapy for precocious puberty; therapy for uterine leiomyoma; early, first trimester abortifacient; therapy for endometriosis; therapy for mammary tumors and cysts; therapy for polycystic ovary syndrome/disease; therapy for uterine carcinoma; therapy for benign prostatic hypertrophy and for prostatic carcinoma; male contraception; therapy for diseases which result from excessive gonadal hormone production in either sex; functional castration in male food producing animals; suppression of proestrous bloody discharge in dogs; diagnostic utilities, such as predisposition to osteoporosis; prevention of ovarian hyperstimulation; preservation of fertility in case of chemotherapy or irradiation; and other uses as set forth in Vickery, B. H., *Endocrine Reviews*, 7:115 (1986), which is fully incorporated by reference herein.

Other features and advantages of the invention will be apparent from the following description of the preferred embodiments thereof, and from the claims.

DESCRIPTION OF THE PREFERRED EMBODIMENTS

Before describing the structure, synthesis, testing, and use of preferred embodiments of the invention, we first describe the drawings.

Structure

The decapeptides of the invention have the general formula recited in the Summary of the Invention above. They all have an acetyl group at the amino terminal end in addition to Ser at position 4. Substitution of non-natural substituents at positions other than $A^2$, $A^3$, and $A^7$ can be used to modify the properties of the compound, and will not prevent the $A^2$, $A^3$, and/or $A^7$ substituents from providing their beneficial effects.

The decapeptides can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, trifluoroacetic, or pamoic acid, as well as polymeric acids such as tannic acid or carboxymethyl cellulose, and salts with inorganic acids such as the hydrohalic acids, e.g., hydrochloric acid, sulfuric acid, or phosphoric acid.

Synthesis

EXAMPLE 1

The synthesis of N-Ac-D-β-Nal-D-Phe-D-Phe-Ser-Try-D-Arg-Phe-Arg-Pro-D-Ala follows.

Other decapeptides of the invention can be prepared by making appropriate modifications of the following synthetic method.

The first step is the preparation of N-Acetyl-D-β-Nal-D-Phe-D-Phe-benzyl-Ser-Tyr-D-tosyl-Arg-Phe-tosyl-Arg-Pro-D-Ala-benzyhdrylamine-resin, as follows.

Benzyhydrylamine-polystyrene resin (Bachem, Inc.) (1.00 g, 0.3 mmole) in the chloride ion form is placed in the reaction vessel of a Beckman 990B peptide synthesizer programmed to perform the following reaction cycle: (a) $CH_2Cl_2$; (b) 33% trifluoroacetic acid in $CH_2Cl_2$ (2 times for 1 and 25 min each); (c) $CH_2Cl_2$; (d) ethanol; (e) $CH_2Cl_2$; (f) triethylamine in $CHCl_3$; and (g) $CH_2Cl_2$.

The neutralized resin is stirred with alpha-t-butoxycarbonyl (Boc)-D-Ala and diisopropylcarbodiimide (1.5 mmole) in CH$_2$Cl$_2$ for 1 hour and the resulting amino acid resin is then cycled through steps (a) to (g) in the above wash program. The following amino acids (1.5 mmole) are then coupled successively by the same procedure: Boc-Pro, Boc-Tosyl-Arg, Boc-Phe, Boc-Tosyl-D-Arg, Boc-Tyr, Boc-benzyl-Ser, Boc-D-Phe, and Boc-D-$\beta$-Nal.

After removal of the N-terminal Boc group, the peptide-benzyhydrylamine resin is neutralized and acetylated by treatment with 5% acetic acid in CH$_2$Cl$_2$. The completed resin is then washed with CH$_3$OH and air dried.

From the above resin is prepared N-Ac-D-$\beta$-Nal-D-Phe-D-Phe-Ser-Tyr-D-Arg-Phe-Arg-Pro-D-Ala, as follows.

A mixture of the above decapeptide resin (1.85 g, 0.5 mmole) and a solution of 4 ml anisole, 100 mg dithiothreitol, and 36 ml hydrogen fluoride is stirred at 0° C. for 45 minutes. Excess hydrogen fluoride is evaporated rapidly under a stream of dry nitrogen, after which the free peptide is precipitated and washed with ether.

The peptide is then dissolved in a minimum volume of 50% acetic ac:,d and eluted on a column (2.5×100 mm) of Sephadex G-25. Fractions containing a major component, as determined by u.v. absorption and thin layer chromatography (tlc), are pooled and evaporated to a small volume in vacuo. This solution is applied to a column (2.5×50 cm) of octadecylsilane-silica (Whatman LRP-1, 15–20 um mesh size) which is eluted with a linear gradient of 15–50% acetonitrile in 20% acetic acid in water. Fractions are examined by tlc and analytical high performance liquid chromatography (hplc) and pooled to give maximum purity. Repeated lyophilization of the solution from water gives 117 mg of the product as a white, fluffy powder.

This material is found to be homogeneous by hplc and tlc. Amino acid analysis of an acid hydrolysate confirms the composition of the decapeptide.

N-Ac-D-$\beta$-Nal-D-p-Cl-Phe-D-Trp-Ser-Phe-D-Arg-Leu-Arg-Pro-D-Ala was prepared according to the synthesis described above, substituting Boc-D-p-Cl-Phe for Boc-D-Phe at position A$^2$, Boc-D-Trp for Boc-D-Phe at position A$^3$, Boc-Phe for Boc-Tyr at position A$^5$, and Boc-Leu for Boc-Phe at A$^7$.

N-Ac-D-$\beta$-Nal-D-p-Cl-Phe-D-Tyr-Ser-Phe-D-Arg-Leu-Arg-Pro-D-Ala was prepared according to the synthesis described above, substituting Boc-D-p-Cl-Phe for Boc-D-Phe at position A$^2$, Boc-D-Tyr for Boc-D-Phe at position A$^3$, Boc-Phe for Boc-Tyr at position A$^5$, and Boc-Leu for Boc-Phe at position A$^7$.

N-Ac-D-$\beta$-Nal-D-Phe-D-Phe-Ser-Phe-D-Arg-Leu-Arg-Pro-D-Ala was prepared according to the synthesis described above, substituting Boc-Phe for Boc-Tyr at A$^5$ and Boc-Leu for Boc-Phe at A$^7$.

EXAMPLE 2

To synthesize peptides featuring D-Lys-$\epsilon$-NH-R at position A$^5$ or Lys-$\epsilon$-NH-R at position 7, where R is an alkyl or aryl group, there is used the method described in Coy, et al., U.S. patent application Ser. No. 879,348, filed June 27, 1986 and assigned to the same assignee as this application, hereby incorporated by reference. In general, the synthesis involves reacting a carbonyl containing compound, e.g., acetone or formaldehyde, with a resin bound polypeptide featuring a Lys or D-Lys subunit in the presence of sodium cyanoborohydride. The carbonyl containing compound reacts with the free $\epsilon$-NH$_2$ group on the side chain of the Lys or D-Lys subunit; reaction with acetone produces an E-N-isopropyl moiety, whereas reaction with formaldehyde produces an $\epsilon$-N-methyl moiety. The synthesis of Ac-D-$\beta$-Nal-D-Phe-D-Phe-Ser-Tyr-D-(isopropyl)Lys-Phe-(isopropyl)Lys-Pro-D-Ala-NH$_2$ follows.

Ac-D-$\beta$-Nal-D-Phe-D-Phe-Ser(Bzl)-Tyr-D-Lys (FMOC)-Phe-D-Lys (FMOC)-Pro-D-Ala-benzyhydrylamine resin (BzL=benzyl; FMOC=fluorenylmethyloxycarbonyl) was prepared by standard methods in a Beckman 990B automatic peptide synthesizer using 33% TFA (trifluoroacetic acid) for removal of the $\alpha$-BOC protecting groups. The $\epsilon$-FMOC protecting groups on the Lys residues are completely stable to these acidic conditions, and to subsequent neutralization steps with 10% triethylamine in chloroform. The resin was then treated with 50 ml of a 50% solution of piperidine in DMF (dimethylformamide) for about 12 h to remove the FMOC protecting groups from the Lys residues.

To react the free $\epsilon$-amino groups of the Lys residues, the resin (0.25 mmole) was mixed with 5 ml of acetone, and 1 mmole of sodium cyanoborohydride in DMF/1% acetic acid added. The resin mixture was then stirred until it was negative to ninhydrin reaction (about 3 h); the negative ninhydrin reaction indicated that the free $\epsilon$-amino groups had been converted to N-isopropyl amino groups.

The resin was then cleaved from the support by treatment with HF/anisole and purified under standard conditions to yield the desired polypeptide.

Ac-D-Nal-D-Phe-D-Phe-Ser-Tyr-D-Lys (isopropyl)-Phe-Arg-Pro-D-Ala-amide is prepared in analogous fashion using appropriate modifications of the above-described procedure.

Testing

A decapeptide of the invention can be tested for its ability to reduce the size of one or more of the following hormone-dependant tumors: the human MCF-7 mammary tumor, the murine MXT or rat MT/W9A-S papillary ductal tumor, and the human DU/145 or rat Dunning R3327 prostate adenocarinoma. The BIM-2000 code numbers used in the Tables and Figures herein refer to the following decapeptides:

| | |
|---|---|
| BIM-21003: | p-Glu—His—Trp—Ser—Tyr-D-Trp—Leu—Arg—Pro—Gly—NH$_2$ |
| BIM-21006: | p-Glu—His—Trp—Ser—Tyr-D-Phe—Leu—Arg—Pro—Gly—NH$_2$ |
| BIM-21009: | N—Ac-D-$\beta$-Nal-D-P—Cl—Phe-D-Phe—Ser—Tyr-D-Arg—Phe—Arg—Pro-D-Ala—NH$_2$ |
| BIM-21011: | N—Ac-D-$\beta$-Nal-D-Phe-D-Phe—Ser—Tyr-D-Arg—Phe—Arg—Pro-D-Ala—NH$_2$ |
| BIM-21023: | N—Ac-D-$\beta$-Nal-D-p-Cl—Phe-D-Trp—Ser—Tyr-D-Arg—Phe—Arg—Pro-D-Ala—NH$_2$ |
| BIM-21024: | N—Ac-D-$\beta$-Nal-D-Phe-D-Phe—Ser—Phe-D-Arg—Leu—Arg—Pro-D-Ala—NH$_2$ |
| BIM-21025: | N—Ac-D-$\beta$-Nal-D-Phe-D-Phe—Ser—Tyr-D-Lys(benzyl)-Phe—Arg—Pro-D-Ala—NH$_2$ |

-continued

BIM-21026: N—Ac-D-β-Nal-D-Phe-D-Phe—Ser—Tyr-D-Lys(cyclopentyl)-Phe—Lys(cyclopentyl)-Pro-D-Ala—NH$_2$ BIM-23014C: D-Nal-Cys—Tyr-D-Trp—Lys—Val—Cys—Thr—NH$_2$.

Human MCF-7 Mammary Tumor

Female CDF-1 mice were implanted with a human mammary tumor (MCF-7) underneath the kidney capsules on day 0. On day 1, animals were injected subcutaneously with BIM-21009, once a day for 6 days. The negative control group received vehicle only and the positive control was ovariectomized on day 0.

Table 1 shows the results of experiment 1, in which daily subcutaneous injections of BIM-21009 (25 ug) over a period of 6 days decreased the size of the tumor to 28% (unless otherwise stated, percentage results are relative to the vehicle-treated control). This effect was similar to that obtained by ovariectomy (−33%). Table 2 shows the results of experiment 2, in which daily subcutaneous injections of BIM-21009 (10 ug) over a period of 6 days decreased the size of the tumor to 28% of the size of the vehicle-treated control tumor. Even at a dose of 1 ug, BIM-21009 reduced the size of the tumor to 53% of the size of the control tumor. These effects were weaker than the effect of ovariectomy on tumor size (tumor reduction to 5% of control size). Table 2 also shows that, at a high dosage, the LHRH superagonists BIM-21003 and BIM-21006 do not desensitize mouse pituitary LHRH receptors. Table 3 shows the results of experiment 3, in which daily subcutaneous injections (2 ug) of the LHRH antagonists BIM-21023, BIM-21024, BIM-21025, and BIM-21026 over a period of 6 days resulted in a decreased tumor size ranging from 29%, 11%, 12%, and 8%, respectively, of the control size. A control peptide which is a somatostatin octapeptide analog, Somatuline (BIM-23014C), at doses of 2 ug, 10 ug, or 50 ug, reduced tumor size to 45%, 32%, and 10%, respectively.

Murine MXT Mammary Papillary Ductal Carcinoma or Rat MT/W9A-S Adenocarcinoma

Female mice or rats were implanted subcutaneously with either murine MXT mammary ductal papillary carcinoma or rat MT/W9A-S mammary adenocarcinoma, respectively, on day 0 and injected once daily subcutaneously with various doses of BIM-21009 from day 1 to day 37. The negative control groups received vehicle only and the positive one was ovariectomized 5 days prior to implanting the tumor.

Figure 1:
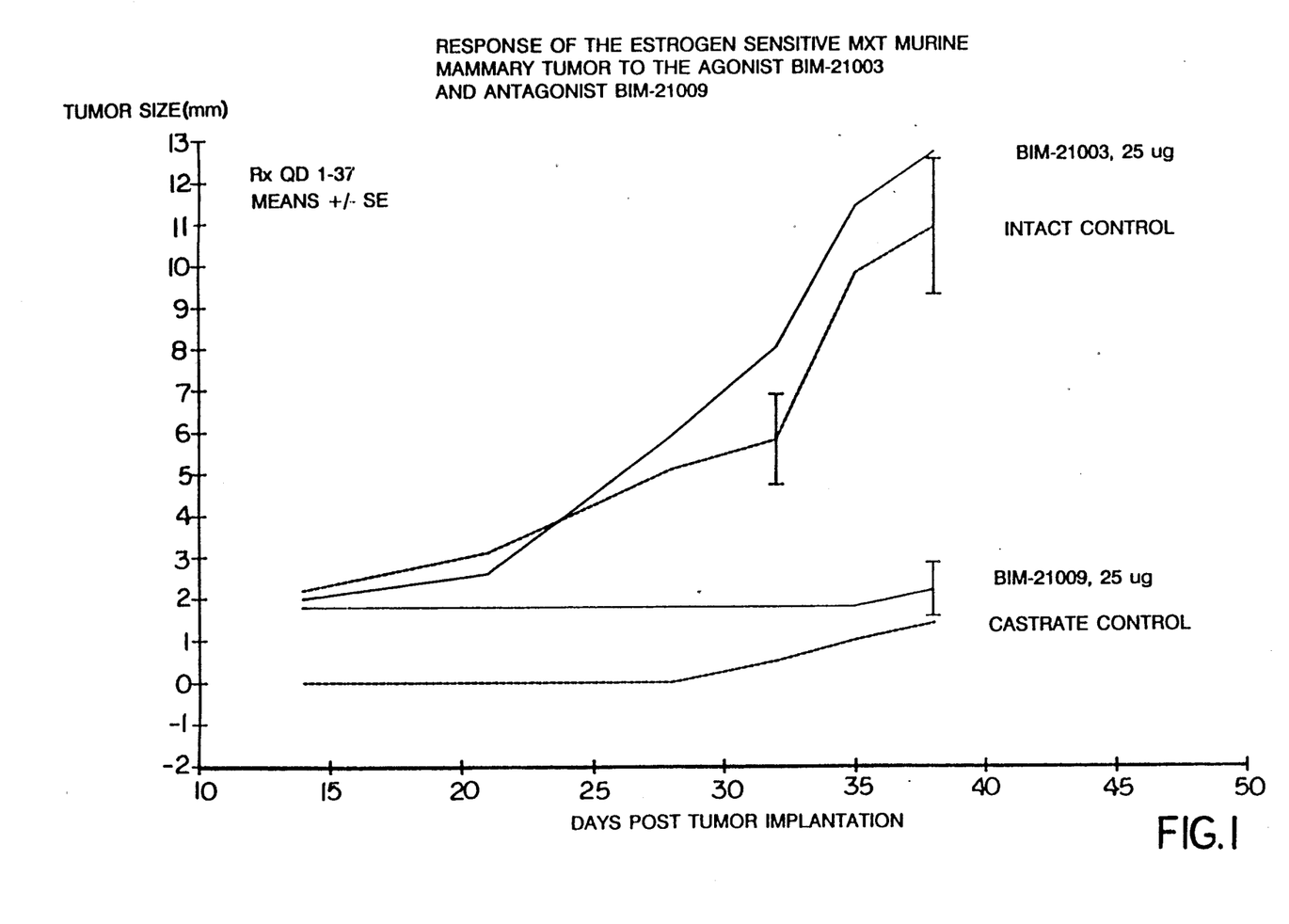
FIG. 1 is a growth curve of the MXT mouse mammary tumor in response to the agonist BIM-21003 and the antagonist BIM-21009.
Figure 2:
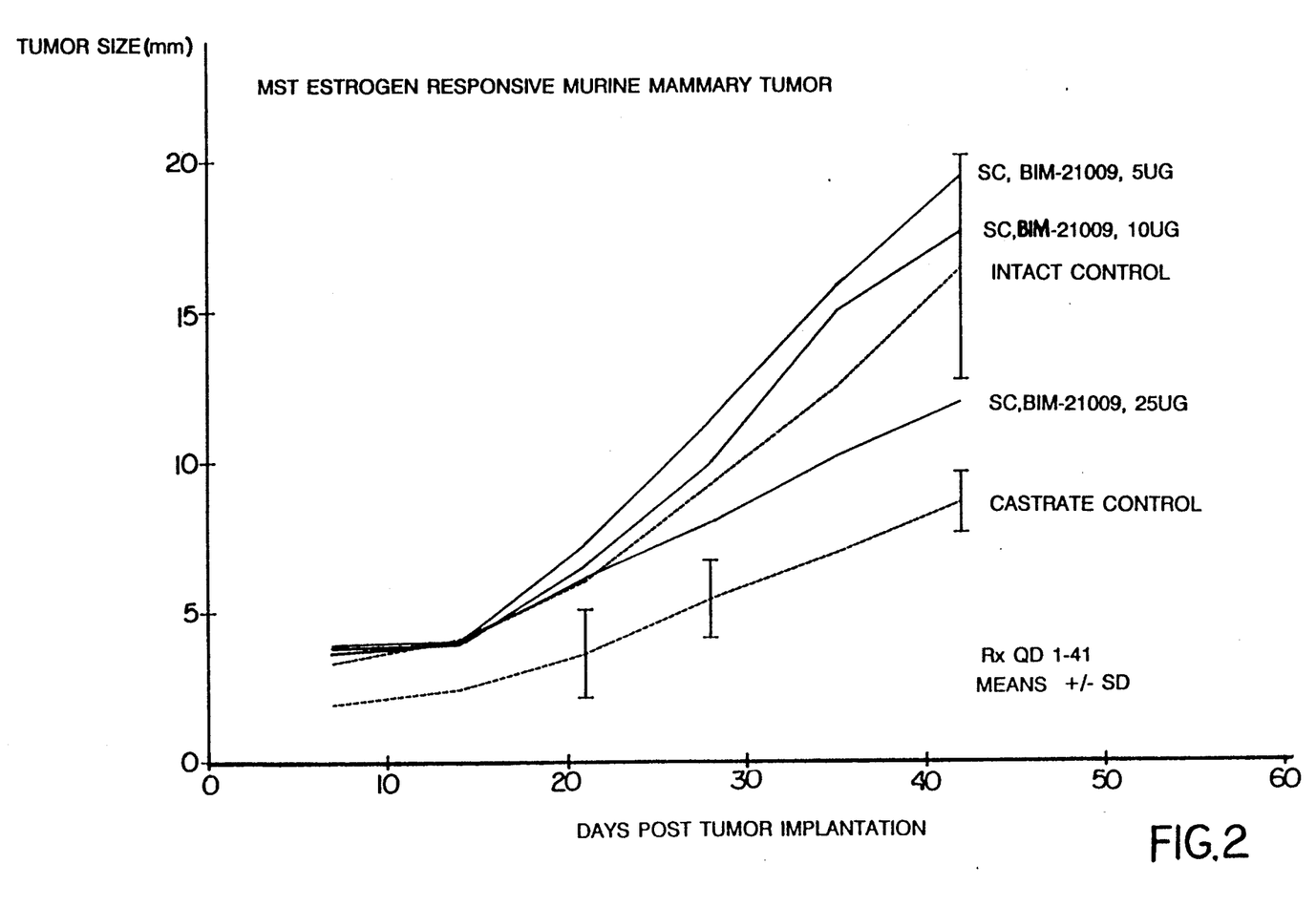
FIG. 2 is a growth curve of the MXT mouse mammary tumor in response to different doses of the antagonist BIM-21009.
Figure 3:
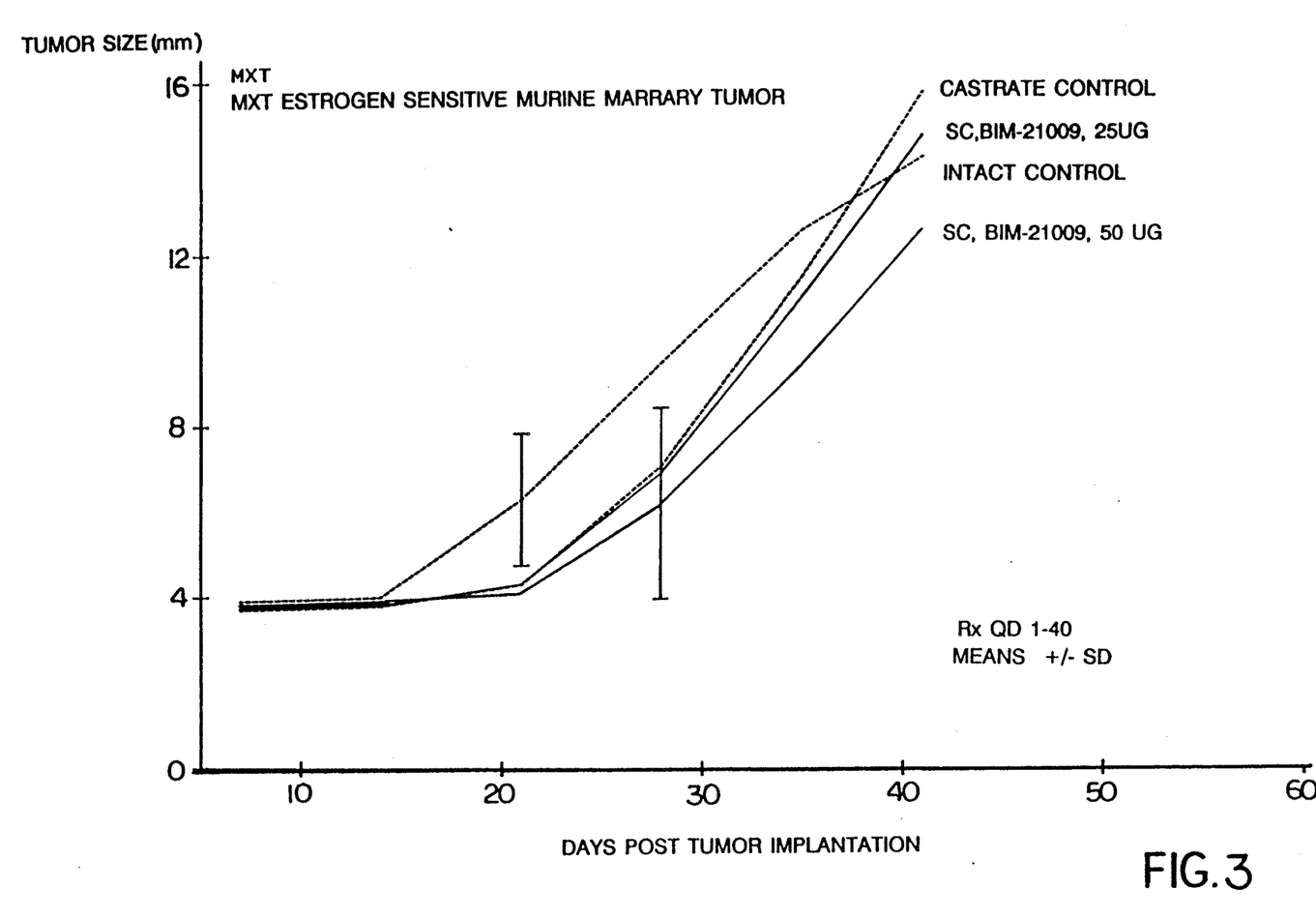
FIG. 3 is a growth curve of the MXT mouse mammary tumor in response to different doses of BIM-21009.
Figure 4:
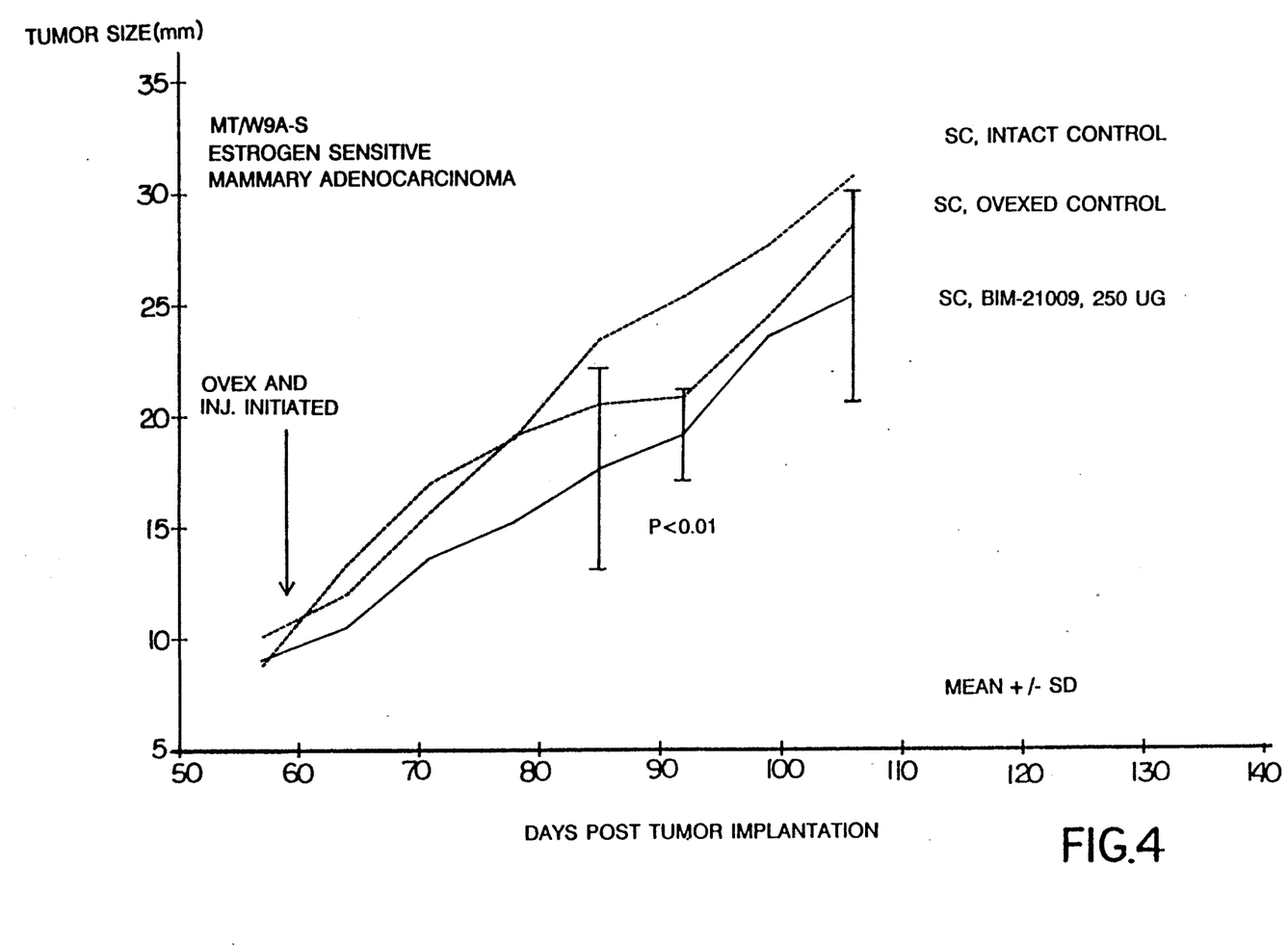
FIG. 4 is a growth curve of the MT/W9A-S mammary adenocarcinoma in response to BIM-21009.

Table 4 and FIG. 1 show that BIM-21009 induced a highly significant tumor growth inhibitory effect (−95%), on MXT estrogen sensitive mammary carcinoma in mice which was better than the effect of ovariectomy on tumor growth (−84%). FIG. 1 also shows the stimulatory effect of the agonist, BIM-21003, on tumor growth since mice pituitary LHRH receptors are not desensitized by LHRH superagonist as opposed to rats or humans. Table 5 shows that BIM-21009 induced a marked reduction in uterus weight (−77%) comparable to that of ovariectomized animals (−85%). Ovaries and pituitary weights were also significantly reduced (−47% and −35%, respectively) FIG. 2 shows that BIM-21009 at a dose of 25 ug significantly reduced tumor size, but not to the extent of castrate control, and demonstrates that the dose of BIM-21009 is proportionate to the size of reduction of the tumor. FIG. 3 shows that the estrogen sensitive MXT murine mammary tumor escapes the growth inhibitory effects of castration, and that BIM-21009 at a dose of 50 ug reduces tumor size and thus retards that escape. FIG. 4 shows that estrogen sensitive rat mammary adenocarcinoma MT/W9A escapes the effects of ovariectomy and that a very high dose of BIM-21009 (250 ug) reduces tumor size and thus retards that escape.

Human DU/145 or Rat Dunning R3327 Prostate Adenocarcinoma

Figure 5:
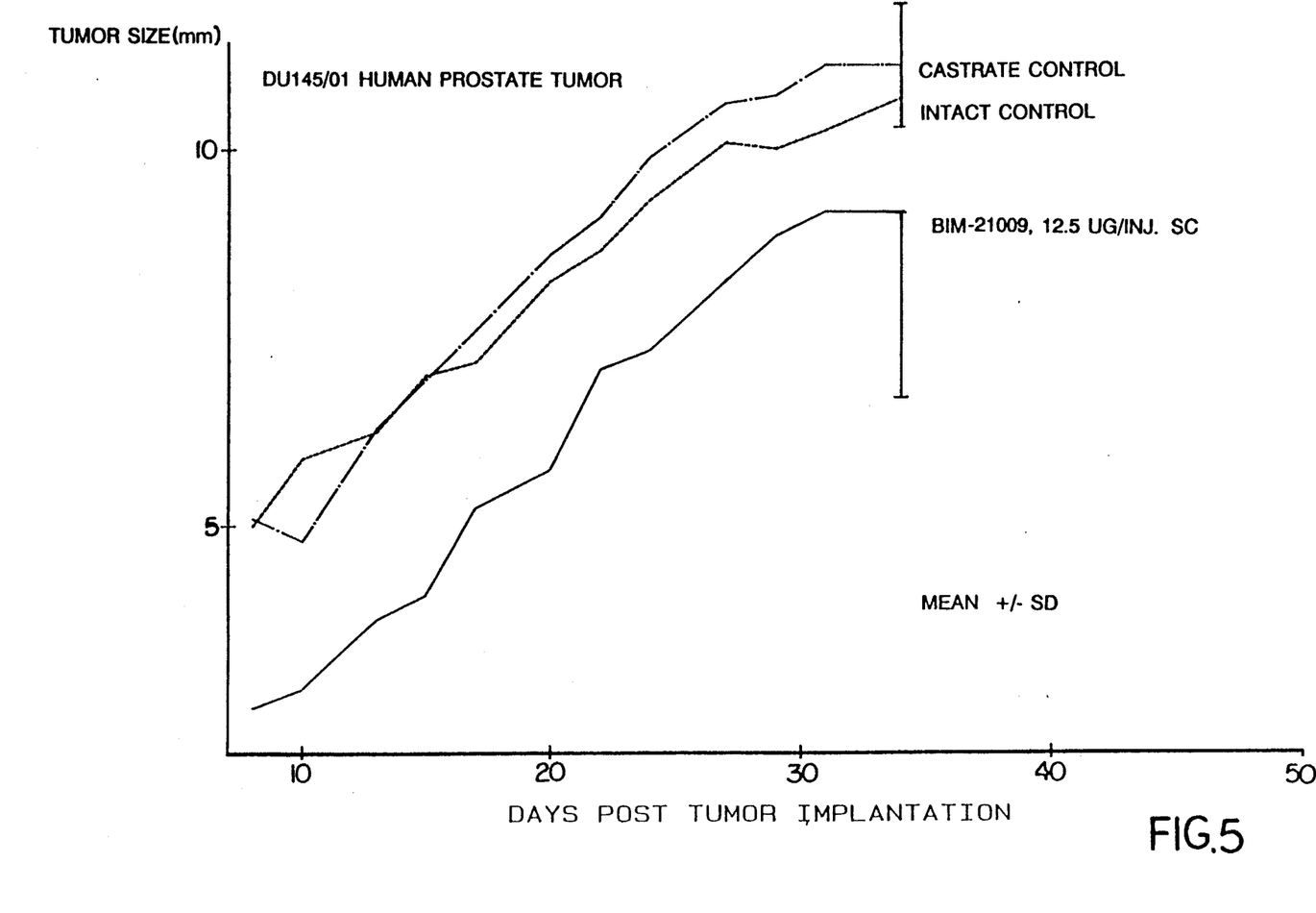
FIG 5 is a growth curve of the DU145/01 human prostate tumor in response to BIM-21009.
Figure 6:
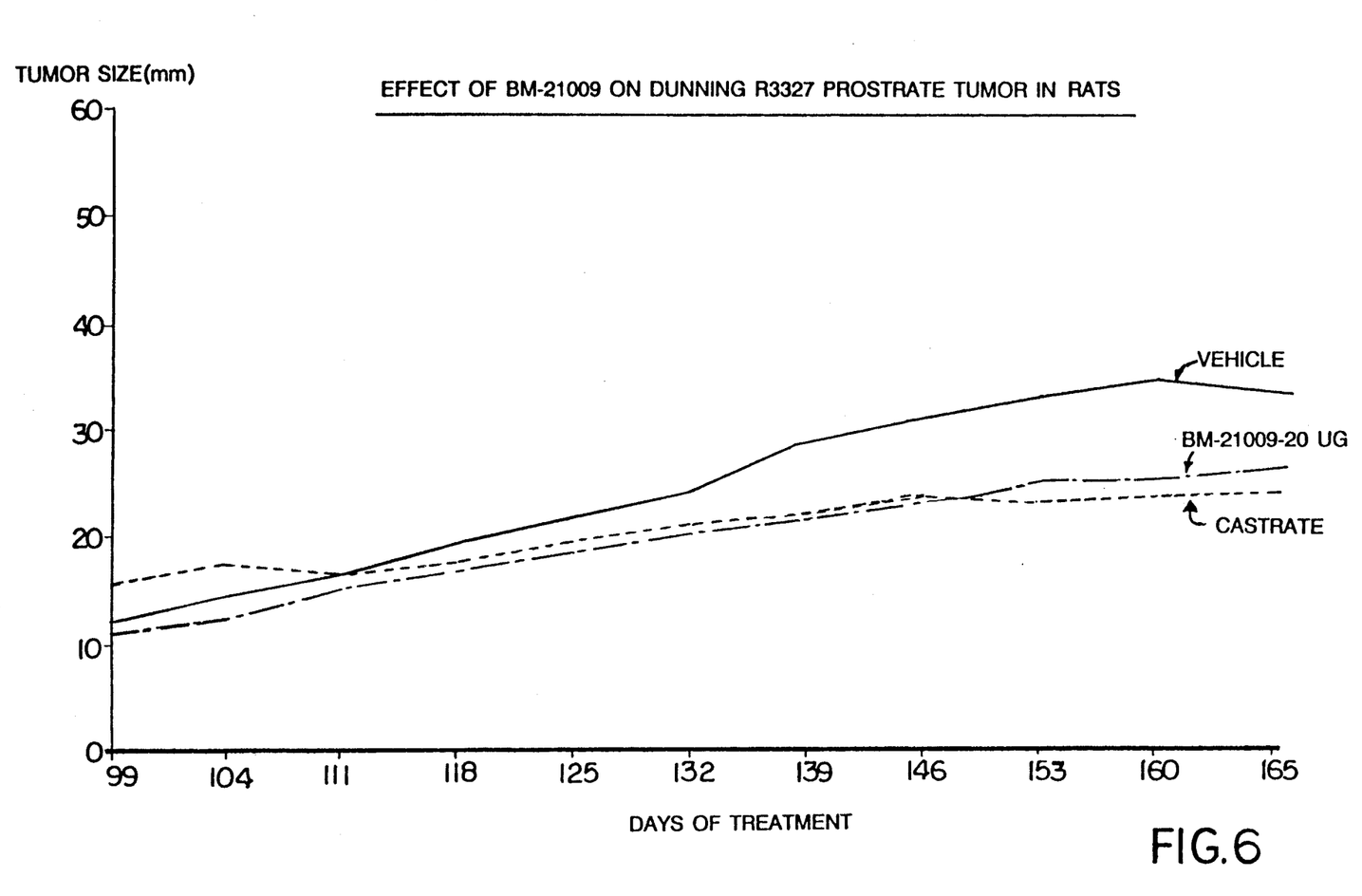
FIG. 6 is a growth curve of the Dunning R3327 prostate tumor in rats in response to BIM-21009.
Figure 7:
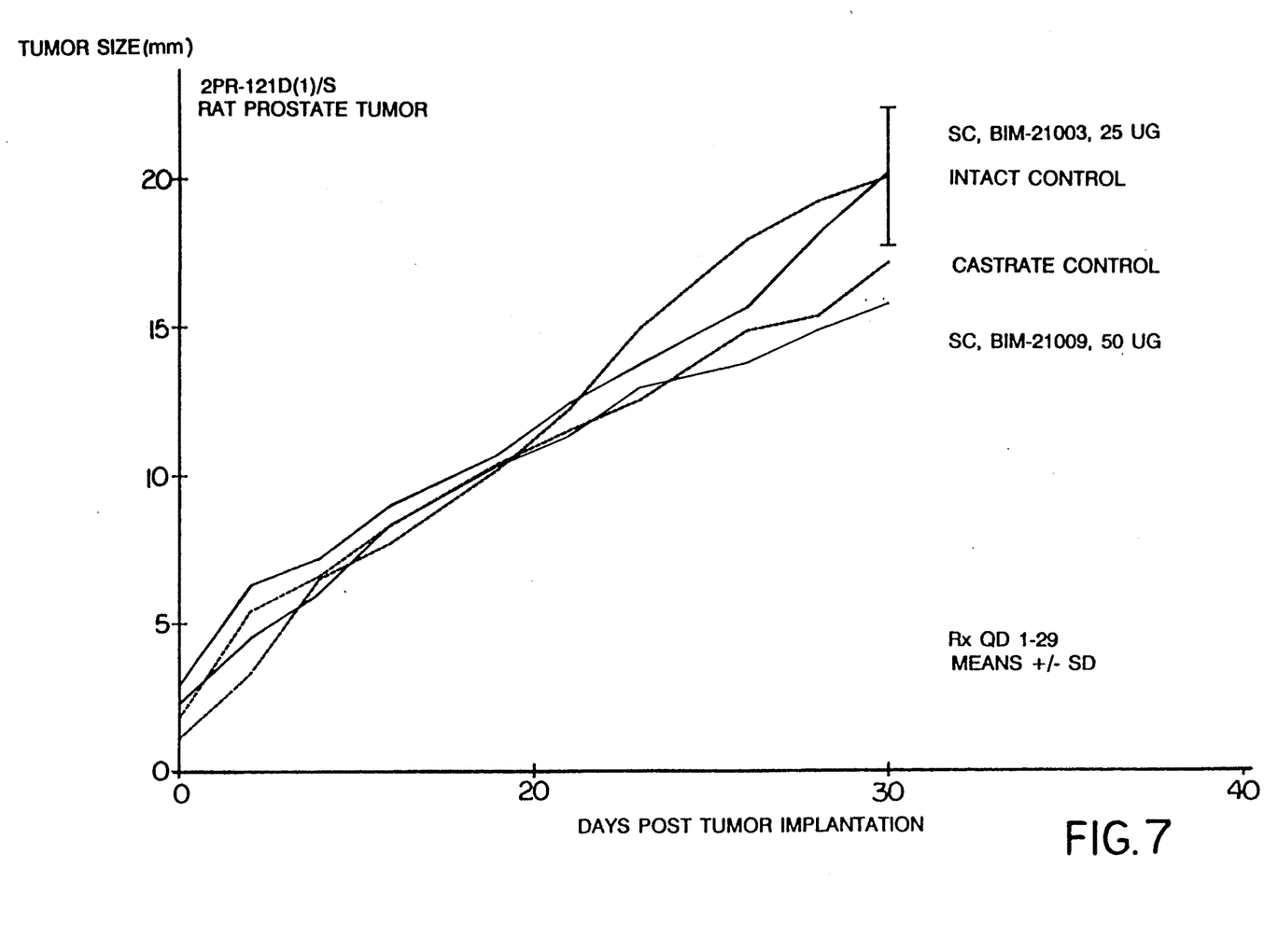
FIG. 7 is a growth curve of the 2PR-121D(1)/S rat prostate tumor in response to BIM-21003 and BIM-21009.
Figure 8:
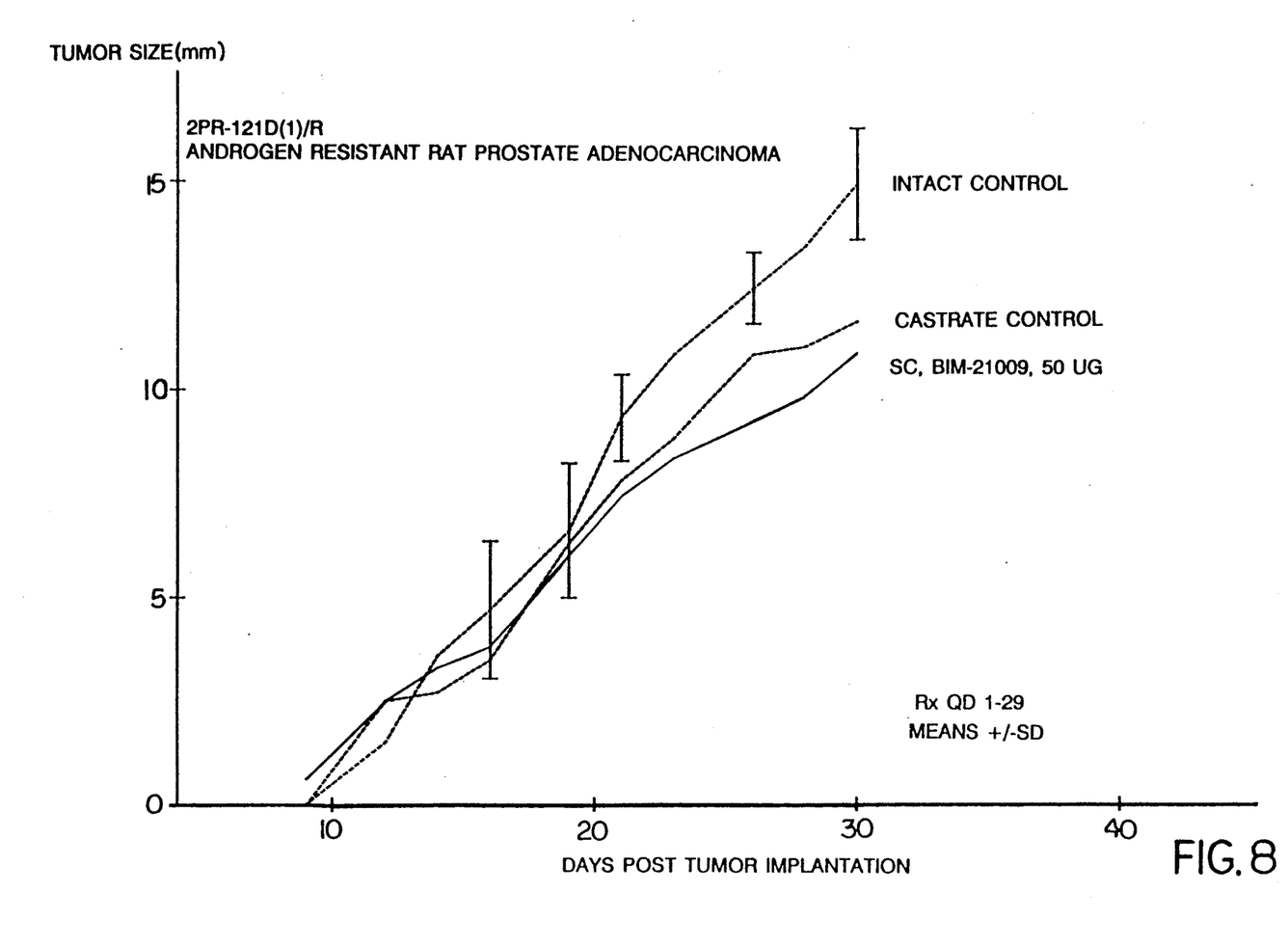

Athymic nude male mice were implanted supercutaneously with xenografts of the human prostate tumor DU/145 and male Copenhagen rats were implanted subcutaneously with the Dunning rat prostate tumor R3327. Negative control groups received vehicle only and positive controls were castrated on day 3 or day 99 post-implant, for the human or rat tumor, respectively. Plasma testosterone levels were determined in the animals at time of sacrifice. The results in FIG. 5 shows that, by day 33 post-implant, BIM-21009 at a dose of 12.5 ug daily for 30 days reduced the average human prostate tumor size significantly, even though the tumor was not responsive to castration. The results in Table 6 and FIG. 6 show that BIM-21009, administered first on day 99 post-implant and then daily, subcutaneously, for 68 days to animals bearing well established growing Dunning R3327 prostate tumors, inhibited tumor growth by 41% at the highest dose tested (20 ug/rat). This effect was weaker than that of castration (−71%). Plasma testosterone levels in these two groups was nil, whereas at a lower dose (5 ug/rat), hormone levels were similar to that observed in the vehicle treated groups (0.87 ng/ml and 0.71 ng/ml, respectively); no significant effect on tumor growth was seen at this dose.

The results in Table 7 show that BIM-21009 at a dose of 20 ug reduced the weight of the whole prostate, the ventral prostate, and the testes (−85%, −53%, and −68%, respectively). BIM-21009 was administered daily for 10 to 30 days post-tumor implant. The results show that the androgen sensitive (2PR-121D(1)/S) and androgen resistant (2PR-121D(1)/R) noble rat prostate tumors both respond to BIM-21009, at a dose of 50 ug, by reduction in tumor size. This reduction is of a greater degree than that observed for the castrate control.

Use

When administered to a mammal (e.g., orally, intravenously, parenterally, nasally, or by suppository), the decapeptides are effective in inhibiting the release of LH induced by LH-RH.

The decapeptides of the invention can be used for the treatment of precocious puberty, hormone dependent tumors (e.g., malignant and benign prostatic, mammary, ovarian and testicular tumors), hirsutism, acne, amenorrhea (e.g., secondary amenorrhea), endometriosis, and ovarian and mammary cystic diseases; the particular decapeptide described above is particularly effective in preventing the growth of mammary tumors. The decapeptides can also be used to regulate human menopausal gonadotropin luteinizing hormone (LH) and follicle-stimulating hormone (FSH) during perimenopausal and postmenopausal periods in women. The decapeptides can also be used as female contraceptives and as an abortifacient.

In general, for the uses herein above described, the decapeptides can be in amounts between about 0.001 and 5 mg/kg body weight. Preferably, for human therapy, the active ingredient will be administered in the range of from about 0.01 to about 1 mg/kg/day, preferably 25-250 mcg/kg/day; and for animal therapy, the active ingredient will be administered in the range of from about 0.1 to 1 mg/kg/day. This administration may be accomplished by a single administration, by distribution over several applications or by slow release in order to achieve the most effective results. Most preferably, for the interruption of heat or prevention of pregnancy in animals, the dose will be in the range of from about 1 to 10 mg/kg, administered as a single dose.

The exact dose and regimen for administration of these compounds and compositions will necessarily be dependent upon the needs of the individual subject being treated, the type of treatment, and the degree of affliction or need. In general, parenteral administration requires lower dosage than other methods of administration which are more dependent upon absorption.

The decapeptides, and LH-RH antagonists in general, can also be used to treat immunosuppressed patients since chemical castration may restore the thymus and thus stimulate the immune system. Examples of additional LH-RH antagonists are described in Coy, U.S. Pat. No. 4,647,653, hereby incorporated by reference, and Coy et al., U.S Pat. No. 4,431,635, previously incorporated by reference. The LH-RH antagonists rejuvenate the thymus when administered as described above.

The compositions may conveniently be administered in unit dosage form and may be prepared by any of the methods well known in the pharmaceutical art, for example, as described in *Remington's Pharmaceutical Sciences*, Mack Publishing Company, Easton, Pa., 1970. Formulations for parenteral administration may contain as common excipients sterile water or saline, alkylene glycols such as propylene glycol, polyalkylene glycols such as polyethylene glycol, oils of vegetable origin, hydrogenated napthalenes and the like. Formulations for vaginal or rectal administration, e.g., suppositories, may contain as excipients, for example, polyalkyleneglycols, vaseline, cocoa butter, and the like. Formulations for nasal administration may be solid and contain as excipients, for example, lactose or dextran, or may be aqueous or oily solutions for administration in the form of nasal drops or metered spray. For buccal administration typical excipients include sugars, calcium stearate, magnesium stearate, pregelatinated starch, and the like.

Nasal administration of the instant nona- and decapeptides is particularly preferred. The absorption across the nasal mucous membrane is enhanced by surfactant acids, such as for example, glycocholic acid, cholic acid, taurocholic acid, cholanic acid, ethocholic acid, desoxycholic acid, chenodesoxycholic acid, dehydrocholic acid, and glycodeoxy-cholic acid.

One or more surfactant acids or salts, but preferably a single pharmaceutically acceptable acid salt, can be added to the LHRH antagonist in solution or powder formulation. Suitable pharmaceutically acceptable surfactant salts will be those salts which retain the phenomenon of enhanced peptide absorption, as well as the compound s surfactant characteristics, and which are not deleterious to the subject or otherwise contraindicated. The amount of surfactant used for the practice of this invention will be some amount which increases the absorption of LHRH peptides over that of other surfactants which also may enhance peptide absorption to a certain degree. It has been found that such an amount is often in the range between 0.2 and 15%, more often 0.2 to 5 percent by weight/volume of the solution. It is preferred that the surfactant be present in an amount between about 0.5 to 4 percent by weight volume, conveniently about 1 percent by weight volume, preferably about 2 percent by weight volume.

Other embodiments are within the following claims.

TABLE 1

EFFECT OF BM-21009 ON MCF-7 HUMAN MAMMARY CARCINOMA GROWTH IN MICE

| Group | Daily Dose per mouse | Change In Tumor Size (mm) | % Variation |
|---|---|---|---|
| Vehicle | — | 0.60 ± 0.54 | — |
| ovariectomized | — | −0.20 ± 0.46** | −33.33 |
| BIM-21009 | 25 μg | −0.17 ± 0.75* | −28.33 |

*p < 0.05
**p < 0.01

TABLE 2

TESTING OF LH-RH AGONISTS AND ANTAGONISTS AGAINST THE TRANSPLANTATION ESTABLISHED MCF-7 HUMAN BREAST TUMOR IN THE 6-DAY SUBRENAL CAPSULE ASSAY

| Group No. | No. Animals | Treatment[1] | | Average Delta Tumor Size[2] (Mean ± S.D.) | % Test/ Control | FBW[3]/IBW |
|---|---|---|---|---|---|---|
| 1 | 10 | Intact-Control, | 0.2 ml/inj. | 2.00 ± 1.47 | — | 0.97 |
| 2. | 9 | Ovexed (Day 0) Vehicle Control | | 0.10 ± 0.80 | 5 | 0.99 |
| 3. | 10 | BIM-21003, | 100 μg/inj. | 2.44 ± 0.98 | 122 | 1.04 |
| 4. | 10 | BIM-21006, | 100 μg/inj. | 1.25 ± 1.39 | 63 | 0.99 |
| 5. | 10 | BIM-21009, | 10 μg/inj. | 0.56 ± 0.85* | 28 | 0.99 |
| 6. | 10 | BIM-21009, | 1 μg/inj. | 1.06 ± 0.83 | 53 | 0.98 |
| 7. | 10 | BIM-21011, | 15 μg/inj. | 0.069 ± 0.61* | 34 | 0.99 |
| 8. | 10 | BIM-210111, | 10 μg/inj. | 1.44 ± 1.21 | 72 | 0.99 |
| 9. | 10 | BIM-21011, | 1 μg/inj. | 1.65 ± 0.71 | 83 | 0.98 |

[1]Control and test compounds were administered s.c. on QDO-5 schedule
[2]Change in tumor size (Day 6 − Day 0) in ocular micrometer units (omu). Significance of difference from intact control: *p < 0.05.
[3]FBW/IBW = Final Body Weight/Intial Body Weight

TABLE 3
COMPARATIVE ACTIVITY OF SOMATULINE (BIM-23014C) AND LH-RH ANTAGONISTS (BIM-21000 TESTED AGAINST THE TRANSPLANTATION ESTABLISHED MCF-7 HUMAN BREAST TUMOR IN THE 6-DAY SUBRENAL CAPSULE ASSAY

| Group No. | No. Animals | Treatment[1] | | Average Delta Tumor Size[2] (Mean ± S.D.) | % Test/ Control | FBW[3]/IBW |
|---|---|---|---|---|---|---|
| 1 | 10 | Intact - Control, 0.2 ml/inj. | | 3.65 ± 2.06 | — | 1.02 |
| 2 | 9 | Ovexed (Day 0) Control, 0.2 ml/inj. | | 1.44 ± 0.55** | 40 | 0.99 |
| 3 | 10 | BIM-23014C, | 50 μg/inj. | 0.35 ± 0.78*** | 10 | 0.98 |
| 4. | 10 | BIM-23014C, | 10 μg/inj. | 1.15 ± 0.95** | 32 | 0.99 |
| 5. | 10 | BIM-23014C, | 2 μg/inj. | 1.65 ± 1.00* | 45 | 1.00 |
| 6. | 10 | BIM-21023, | 25 μg/inj. | 1.05 ± 1.13** | 29 | 1.01 |
| 7. | 10 | BIM-21024, | 25 μg/inj. | 0.04 ± 0.77*** | 11 | 1.00 |
| 8. | 10 | BIM-21025, | 25 μg/inj. | 0.45 ± 0.76*** | 12 | 0.97 |
| 9. | 10 | BIM-21026, | 25 μg/inj. | 0.30 ± 0.46*** | 8 | 1.01 |

[1] Vehicle Control and BIM-23014C groups were administered s.c. on QDO-5, b.i.d. schedule. All other test materials were administered s.c. on a QDO-5 schedule.
[2] Change in tumor size (Day 6 − Day 0) in ocular micrometer units (omu). Significance of difference from intact control: *p < 0.05; p < 0.01; *p < 0.001.
FBW/IBW = Final Body Weight/Initial Body Weight

TABLE 4
EFFECT OF BM-21009 ON MXT MAMMARY CARCINOMA GROWTH IN MICE

| Group | Daily Dose per mouse | Tumor Size (mm) Day 14 | Tumor Size (mm) Day 38 | Tumor Increase | % Variation |
|---|---|---|---|---|---|
| Vehicle | — | 2.2 ± 0.64 | 10.9 ± 1.63 | 8.7 | — |
| ovariectomized | — | 0 | 1.4 ± 0.70*** | 1.4 | −83.91 |
| BM-21009 | 25 μg | 1.8 ± 0.66 | 2.2 ± 0.64*** | 0.4 | −95.40 |

***p < 0.001

TABLE 5
EFFECT OF BM-21009 ON ENDOCRINE ORGANS OF MXT TUMOR BEARING MICE

| Group | Pituitary | Adrenals | Uteri | Ovaries |
|---|---|---|---|---|
| Vehicle | 2.31 ± 0.23 | 8.10 ± 0.54 | 76.97 ± 11.40 | 15.46 ± 0.74 |
| ovariectomized | 2.13 ± 0.14 | 6.78 ± 0.15* | 11.25 ± 0.67*** | — |
| % Variation | −7.79 | −16.30 | −85.38 | |
| BM-21009 25 μg/day | 1.50 ± 0.08 | 8.90 ± 0.27 | 17.69 ± 1.00*** | 8.14 ± 0.58*** |
| % Variation | −35.06 | 0 | −77.02 | −47.35 |

*p < 0.05
**p < 0.01
***p < 0.001

TABLE 6
EFFECT OF BM-21009 ON DUNNING R3327 PROSTATE ADENOCARCINOMA GROWTH IN RATS

| Group | Daily Dose per Rat | Tumor Size (mm) Day 99 | Tumor Size (mm) Day 165 | Tumor Increase | % Variation |
|---|---|---|---|---|---|
| Vehicle | — | 11.80 ± 2.33 | 34.00 ± 5.05 | 22.20 | — |
| Castrate | — | 15.40 ± 1.66 | 21.80 ± 2.09 | 6.40 | −71.17 |
| BM-21009 | 20 μg | 11.00 ± 2.51 | 24,10 ± 2.22 | 13.100 | −40.99 |
| | 5 μg | 11.20 ± 1.29 | 28.90 ± 3.48 | 17.70 | −20.27 |

TABLE 7
EFFECT OF BM-21009 ON ENDOCRINE ORGANS IN R3327 PROSTATE TUMOR BEARING RATS

| Organ Weights | Vechicle | Castrate | BM-21009 20 μg | BM-21009 5 μg |
|---|---|---|---|---|
| Whole Prostate (mg) | 265 ± 48 | 29 ± 4 | 41 ± 19 | 245 ± 31 |
| % Variation | — | −89.06 | −84.53 | −7.55 |
| Ventral Prostate (mg) | 55 ± 17 | 15 ± 3 | 26 ± 8 | 64 ± 9 |
| % Variation | — | −72.73 | −52.73 | +16.36 |
| Testes (g) | 2.03 ± 0.17 | — | 0.65 ± 0.43 | 1.8 ± 0.1 |
| % Variation | — | — | −67.98 | −11.33 |
| Adrenals (mg) | 34 ± 2 | 29 ± 4 | 33 ± 1 | 32 ± 2 |
| % Variation | — | −14.71 | −2.94 | −5.88 |
| Pituitary (mg) | 7.3 ± 0.6 | 7.2 ± 0.9 | 6.5 ± 0.2 | 7.0 ± 0.8 |

TABLE 7-continued

| EFFECT OF BM-21009 ON ENDOCRINE ORGANS IN R3327 PROSTATE TUMOR BEARING RATS | | | |
|---|---|---|---|
| Organ Weights | Vechicle | Castrate | BM-21009 20 μg | BM-21009 5 μg |
| % Variation | — | −1.37 | −10.96 | −4.11 |

What is claimed:

1. A decapeptide of the formula:

$$\text{N-Ac-}A^1\text{-}A^2\text{-}A^3\text{-Ser}^4\text{-}A^5\text{-}A^6\text{-}A^7\text{-}A^8\text{-}A^9\text{-}A^{10},$$

wherein each $A^1$, $A^2$, and $A^3$, independently, is D-$\beta$-Nal, D-p-X-Phe (where X is halogen, H, $NH_2$, $NO_2$, OH, or $C_{1-3}$ alkyl); $A^5$ is p-X-Phe (where X is halogen, H, $NH_2$, $NO_2$, OH, or $C_{1-3}$ alkyl); $A^6$ is D-Lys, D-Arg, $\beta$-Nal, D-$\beta$-Nal, D-Trp, D-p-X-Phe (where X is halogen, H, $NH_2$, $NO_2$, OH, or $C_{1-3}$ alkyl) or D-Lys-$\epsilon$-NH-R (where R is H, a branched or straight chain or cyclo $C_1$-$C_{10}$ alkyl group, or an aryl group); $A^7$ is p-X-Phe (where X is halogen, H, $NH_2$, $NO_2$, OH, $C_2F_5$, or $C_{1-3}$ alkyl), cyclohexylalanine, or Trp; $A^8$ is Arg, Lys, or Lys-$\epsilon$-NH-R (where R is H, a branched or straight chain or cyclo $C_1$-$C_{10}$ alkyl group, or an aryl group); $A^9$ is Pro; and $A^{10}$ is D-Ala-$NH_2$, Gly-$NH_2$, D-Ser, or D-Ser-$NH_2$; provided that at least one of $A^2$ or $A^3$ must be D-Phe or D-Tyr; and further provided that one or both of $A^6$ and $A^8$ must be the following: $A^6$ is D-Lys-$\epsilon$-NH-R (where R is H, a branched or straight chain or cyclo $C_1$-$C_{10}$ alkyl group, or an aryl group); $A^8$ is Lys-$\epsilon$-NH-R (where R is H, a branched or straight chain or cyclo $C_1$-$C_{10}$ alkyl group, or an aryl group), or a pharmaceutically acceptable salt thereof.

2. The decapeptide of claim 1 wherein $A^6$ is D-Lys-$\epsilon$-NH-R (where R is H a branched or straight chain or cyclo $C_{1-10}$ alkyl group, or an aryl group).

3. The decapeptide of claim 1 or 2 wherein $A^8$ is Lys-$\epsilon$-NH-R (where R is H, a branched or straight chain or cyclo $C_1$-$C_{10}$ alkyl group, or an aryl group).

4. The decapeptide of claim 2 wherein $A^1$–$A^{10}$ is N-acetyl-D-$\beta$-Nal-D-Phe-D-Phe-Ser-Tyr-D-Arg-Phe-(isopropyl)D-Lys-Pro-D-Ala-$NH_2$.

5. The decapeptide of claim 2 wherein $A^1$–$A^{10}$ is N-acetyl-D-$\beta$-Nal-D-Phe-D-Phe-Ser-Tyr-D-Lys(benzyl)-Phe-Arg-Pro-D-Ala-$NH_2$.

6. The decapeptide of claim 2 wherein $A^1$–$A^{10}$ is N-acetyl-D-$\beta$-Nal-D-Phe-D-Phe-Ser-Tyr-D-Lys(Cl-benzyl)-Phe-Arg-Pro-D-Ala-$NH_2$.

7. The decapeptide of claim 2 wherein $A^1$–$A^{10}$ is N-acetyl-D-$\beta$-Nal-D-Phe-D-Phe-Ser-Tyr-D-Lys(heptyl)-Phe-Arg-Pro-D-Ala-$NH_2$.

8. The decapeptide of claim 2 wherein $A^1$–$A^{10}$ is N-acetyl-D-$\beta$-Nal-D-Phe-D-Phe-Ser-Tyr-D-Lys(cyclo-pentyl)-Phe-Arg-Pro-D-Ala-$NH_2$.

9. The decapeptide of claim 3 wherein $A^1$–$A^{10}$ is N-acetyl-D-$\beta$-Nal-D-Phe-D-Phe-Ser-Tyr-D-Arg-Phe-Lys (t-butylmethyl)-Pro-D-Ala-$NH_2$.

10. The decapeptide of claim 3 wherein $A^1$–$A^{10}$ is N-acetyl-D-$\beta$-Nal-D-Phe-D-Phe-Ser-Tyr-D-Arg-Phe-Lys (4-methyl-benzyl)-Pro-D-Ala-$NH_2$.

11. The decapeptide of claim 3 wherein $A^1$–$A^{10}$ is N-acetyl-D-$\beta$-Nal-D-Phe-D-Phe-Ser-Tyr-D-Arg-Phe-Lys (benzyl)-Pro-D-Ala-$NH_2$.

12. The decapeptide of claim 3 wherein $A^1$–$A^{10}$ is N-acetyl-D-$\beta$-Nal-D-p-Cl-Phe-D-Trp-Ser-Tyr-D-p-$NH_2$-Phe-Phe-(isopropyl)Lys-Pro-D-Ala-$NH_2$.

13. The decapeptide of claim 3 wherein $A^1$–$A^{10}$ is N-acetyl-D-$\beta$-Nal-D-Phe-D-Phe-Ser-Tyr-D-Lys(heptyl)-Phe-Lys (heptyl)-Pro-D-Ala-$NH_2$.

14. The decapeptide of claim 3 wherein $A^1$–$A^{10}$ is N-acetyl-D-$\beta$-Nal-D-Phe-D-Phe-Ser-Tyr-D-Lys(cyclopentyl)-Phe-Lys(cyclopentyl)-Pro-D-Ala-$NH_2$.

15. The decapeptide of claim 3 wherein $A^1$–$A^{10}$ is N-acetyl-D-$\beta$-Nal-D-Phe-D-Phe-Ser-Tyr-D-Lys(1-butylpentyl)-Phe-Lys(1-butylpentyl)-Arg-Pro-D-Ala-$NH_2$.

16. A therapeutic composition for inhibiting the LH-RH induced release of sex hormones comprising a therapeutically effective amount of the decapeptide of claim 1 together with a pharmaceutically acceptable carrier substance.

17. A method of treating a mammal in need of inhibition of LH-RH induced release of sex hormones comprising administering to said mammal a therapeutically effective amount of the decapeptide of claim 1.

18. The composition of claim 16 wherein said composition is in the form of a pill, tablet, capsule, liquid, or sustained release tablet for oral administration to a patient in need of said decapeptide.

19. The composition of claim 16 wherein said composition is in the form of a liquid capable of being administered intravenously, subcutaneously, parenterally, topically, or intraperitoneally to a patient in need of said decapeptide.

20. The composition of claim 16 wherein said composition is in the form of an injectible suspension comprising said decaptide and a bioerodible, biocompatible polymer matrix capable of effecting sustained release of said decapeptide.

21. The composition of claim 16 wherein said composition is in the form of a decapeptide/bioerodible, biocompatible implant.

22. The composition of claim 16 wherein said composition is a transdermal patch or transmucosal patch, or a nasal spray.

* * * * *